(12) United States Patent
Chen et al.

(10) Patent No.: US 11,138,730 B2
(45) Date of Patent: Oct. 5, 2021

(54) VISIBLE CEPHALOMETRIC MEASUREMENT METHOD, SYSTEM AND COMPUTER PROCESSING DEVICE

(71) Applicant: Fussen Technology Co., Ltd., Shenzhen (CN)

(72) Inventors: Minfeng Chen, Shenzhen (CN); Jing Lei, Shenzhen (CN)

(73) Assignee: FUSSEN TECHNOLOGY CO., LTD., Shenzhen (CN)

( * ) Notice: Subject to any disclaimer, the term of this patent is extended or adjusted under 35 U.S.C. 154(b) by 72 days.

(21) Appl. No.: 16/108,011

(22) Filed: Aug. 21, 2018

(65) Prior Publication Data

US 2019/0073771 A1    Mar. 7, 2019

(30) Foreign Application Priority Data

Sep. 1, 2017    (CN) .......................... 201710780875.1
Nov. 2, 2017    (CN) .......................... 201711062524.3

(51) Int. Cl.
     *A61B 6/00*        (2006.01)
     *G06T 7/00*        (2017.01)
     (Continued)

(52) U.S. Cl.
CPC .......... *G06T 7/0014* (2013.01); *A61B 6/501* (2013.01); *A61B 6/5211* (2013.01); *G06T 2207/10116* (2013.01); *G06T 2207/30008* (2013.01)

(58) Field of Classification Search
CPC ............... A61B 6/501; A61B 6/5211; G06T 2207/10116; G06T 2207/3008; G06T 7/0014
See application file for complete search history.

(56) References Cited

U.S. PATENT DOCUMENTS 4,528,627 A * 7/1985 Coben ................. A61B 5/107
                                                128/924
5,342,202 A * 8/1994 Deshayes ............. A61B 5/107
                                                433/215
(Continued)

OTHER PUBLICATIONS

Bing Li, "Computerable Ricketts analysis system and establishment of static VTO correction setting system", data base for excellent MA theses of China, Series of Medicine and Health Science, Li Bing, issue of No. 12, p. E074-47 and section 2 of pp. 23-28, Dec. 15, 2009.

(Continued)

*Primary Examiner* — Soo Shin
(74) *Attorney, Agent, or Firm* — Hemisphere Law, PLLC; Zhigang Ma

(57) ABSTRACT

A method for visible cephalometric measurement is provided. The method comprises: acquiring a data item to be measured according to a preset analysis method, and acquiring preset reference information; determining a measurement reference point according to the acquired preset reference information; and generating a measurement result based on the measurement reference point and the data item to be measured, and displaying it. A computer processing device and a visible cephalometric system are also provided. The computer may automatically generate measurement results according to user's selection and perform cephalometric measurement more easily, accurately, and more efficiently.

9 Claims, 6 Drawing Sheets

(51) Int. Cl.
    *G06T 7/60*         (2017.01)
    *G06T 7/70*         (2017.01)
    *G16H 50/20*       (2018.01)

(56) References Cited

U.S. PATENT DOCUMENTS

| | | | |
|---|---|---|---|
| 10,758,322 B2* | 9/2020 | Pokotilov | A61C 7/08 |
| 10,898,298 B1* | 1/2021 | Raslambekov | A61C 7/002 |
| 10,937,250 B2* | 3/2021 | Xie | G06T 17/20 |
| 2011/0244415 A1* | 10/2011 | Batesole | A61C 7/00 433/24 |
| 2011/0268326 A1* | 11/2011 | Kuo | G06T 7/33 382/128 |
| 2013/0217996 A1* | 8/2013 | Finkelstein | A61B 5/1075 600/407 |
| 2014/0348405 A1* | 11/2014 | Chen | G06T 7/75 382/131 |
| 2016/0203604 A1* | 7/2016 | Gupta | A61C 7/002 382/128 |
| 2017/0258420 A1* | 9/2017 | Inglese | A61B 6/501 |
| 2018/0061054 A1* | 3/2018 | Abraham | A61B 6/501 |
| 2018/0147015 A1* | 5/2018 | She | G06T 5/002 |
| 2018/0184989 A1* | 7/2018 | Inglese | A61B 6/5217 |
| 2018/0314797 A1* | 11/2018 | Madan | G06N 20/00 |
| 2019/0073771 A1* | 3/2019 | Chen | A61B 6/5211 |
| 2019/0328489 A1* | 10/2019 | Capron-Richard | G06T 7/0012 |
| 2020/0035351 A1* | 1/2020 | Kim | G16H 50/30 |

OTHER PUBLICATIONS

Guotao Yu, "Design of cephalometric analysis system for orthodontics", data base for excellent MA theses of China, Series of Medicine and Health Science, Guotao Yu, the fourth issue, p. E074-1 and p. 60, Apr. 15, 2015.

* cited by examiner

VISIBLE CEPHALOMETRIC MEASUREMENT METHOD, SYSTEM AND COMPUTER PROCESSING DEVICE

TECHNICAL FIELD

The present invention relates to the field of computer technologies, and in particular, to a method for visible cephalometric measurement, system, and computer processing device.

BACKGROUND

X-ray cephalometric measurement is mainly to measure the image obtained by cephalometric X-ray radiography. A certain line angle is drawn on individual marked points of dental jaw and craniofacial regions for measurement and analysis, so as to understand the structure of dental jaw and craniofacial soft and hard tissues. During the inspection, it is found that whether there are abnormal shadows and patterns, so that the inspection and diagnosis of the dental jaws and craniofacial surface could go from surface morphology deeper into the internal skeletal structure. It is of great significance for the study of craniofacial growth and development, the diagnostic analysis of dental jaw and craniofacial deformity, the determination of corrective design of malocclusion, the investigation of morphological changes of dental jaws and craniofacial surface during and after the orthodontics processes, the correction effect of surgical orthodontic prediction surgery, and the analysis of mandibular function.

The X-ray cephalometric measurement technique currently uses manual drawing and measurement stages. In the process of manually plotting and measuring, cephalometric measurement needs to depict the X-ray head-image of the film on sulfuric acid paper on a dedicated tracing table, and then perform measurement analysis on the tracing paper. This method is cumbersome; the located point is not clear; the error is large; and the requirements for the operator are relatively high.

Therefore, it becomes an urgent problem in the field to provide a method for visible cephalometric measurement to perform cephalometric measurement more easily, accurately and efficiently.

SUMMARY

It is one object of the present invention to provide a method for visible cephalometric measurement that makes cephalometric measurement easier, more accurately and more efficiently.

In order to achieve the above objects, an embodiment of the present invention discloses a method for visible cephalometric measurement. The method comprises:
  acquiring a data item to be measured according to a preset analysis method, and acquiring preset reference information;
  determining a measurement reference point according to the acquired preset reference information; and
  generating a measurement result based on the measurement reference point and the data item to be measured, and displaying it.

Preferably, the preset analysis method comprises at least one of Tweed analysis method, Downs analysis method, Steiner analysis method, Wylie analysis method, Coben analysis method, Ricketts analysis method, quadrangular analysis method and soft tissue analysis method.

Preferably, the preset analysis method includes a custom analysis method, which is determined according to a preset measurement data item.

Preferably, the preset reference information includes a preset reference point and a name of the preset reference point; the step of determining the measurement reference point according to the acquired preset reference information further includes:
  marking a preset reference point on a trace diagram according to the preset reference point name;
  obtaining the reference point marked on an X-ray photograph and marking it on the corresponding reference point name.

Preferably, the method further includes: marking a next preset reference point on the trace diagram according to a next preset reference point name.

Preferably, after the step of obtaining the reference point marked on the X-ray photograph, the method further includes: acquiring a coordinate value of the reference point.

A computer processing device including a processor and a computer-readable storage medium is provided according to another embodiment of the present invention. The processor acquires a computer program on the computer-readable storage medium and executes the method according to any one of the above methods.

A visible cephalometric system according to another embodiment of the present invention. The system comprises:
  an acquiring unit, for acquiring a data item to be measured according to a preset analysis method, and acquiring preset reference information;
  a determining unit, for determining a measurement reference point according to the acquired preset reference information; and
  a processing unit, for generating a measurement result according to the measurement reference point and the data item to be measured, and displaying it.

Preferably, the preset reference information includes a preset reference point and a name of the preset reference point; and the determining unit is configured to: mark a preset reference point on a trace diagram according to the preset reference point name; obtain the reference point marked on an X-ray photograph and marking it on the corresponding reference point name.

Preferably, the system further includes: a display unit, for displaying the X-ray photograph, the trace diagram, the data item to be measured, the reference point name, and the measurement result.

In this way, according to the analysis method selected by the user, the data item to be measured is determined, the preset reference information is acquired, then the measurement reference point is determined according to the acquired preset reference information, and the measurement result is generated according to the measurement reference point and the measurement data item to be measured, and displays them, so that the computer may automatically generate measurement results and perform cephalometric measurement more easily, accurately, and more efficiently. When it is used, the user only needs to select the analysis method, and the system may determine the data items to be measured and the preset reference information according to the analysis method selected by the user, so as to prompt the reference point and other information for the user to select. After the user determines, the reference point and other information may be referred for measurement, and the measurement results are obtained.

DETAILED DESCRIPTION

Figure 1:
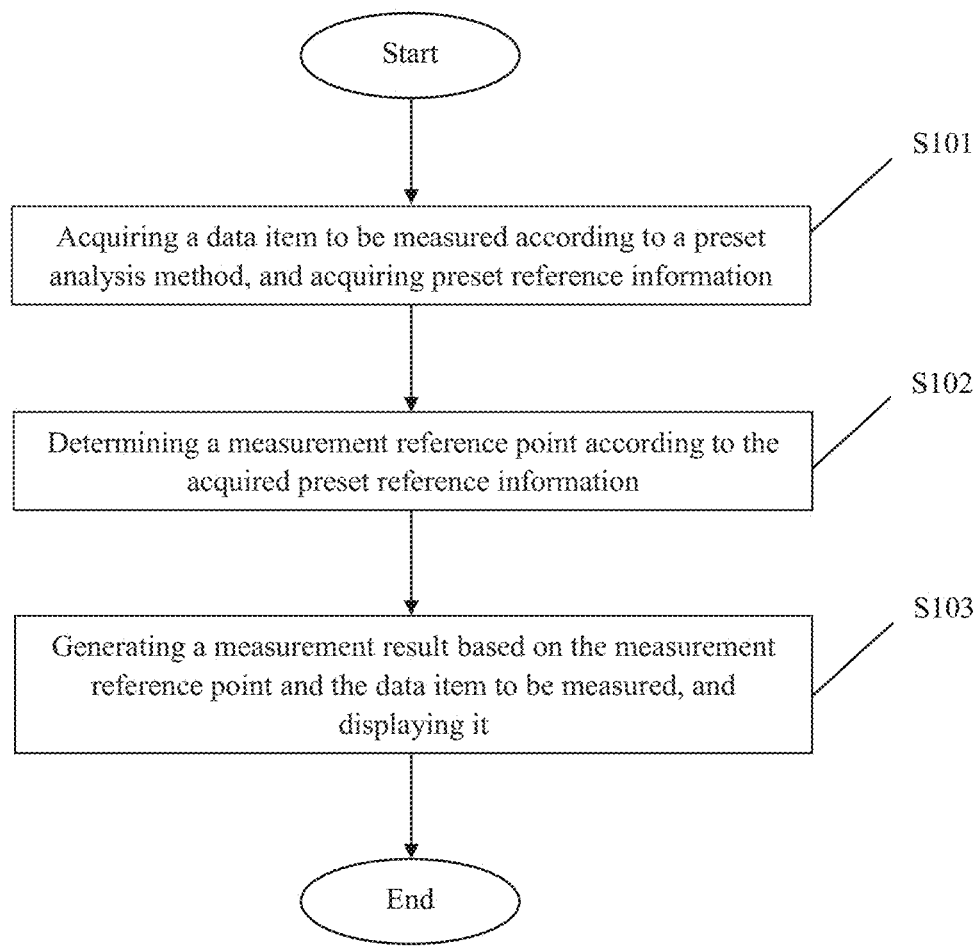
FIG. 1 is a flowchart of a method for visible cephalometric measurement according to an embodiment of the present invention.

Although a flowchart describes the operations as a sequential process, many of these operations may be performed in parallel, concurrently or simultaneously. The order of operations may be rearranged. The process may be terminated when its operation is completed, but it may also have additional steps not included in the drawings. The processes could correspond to methods, functions, procedures, subroutines, subprograms, and so on.

A computer device includes a user equipment and a network equipment. The user equipment or the client includes but is not limited to a computer, a smart phone, a PDA, and the like; the network equipment includes but is not limited to a single network server, a server group composed of a plurality of network servers, or a cloud-based computing cloud consisting of a large number of computers or network servers. The computer device may operate individually to implement the present invention, and may also access the network and implement the invention by interacting with other computer devices in the network. The network in which the computer equipment is located includes, but is not limited to, the Internet, a wide area network (WAN), a metropolitan area network (MAN), a local area network (LAN), a VPN network, and the like.

The terms "first," "second," etc. may be used herein to describe various elements, but the elements should not be limited by these terms, and these terms are used merely to distinguish one element from another. As used herein, the term "and/or" includes any and all combinations of one or more of the listed associated items. When a unit is referred to as being "connected" or "coupled" to another unit, it may be directly connected or coupled to the other unit or may be connected or coupled to the other unit via an intermediate unit.

The terminology used herein is only for the purpose of describing particular embodiments and is not intended to limit exemplary embodiments. As used herein, the singular forms "a," "an," and "the" may be intended to include the plural forms as well, unless the context clearly indicates otherwise. It should also be understood that the terms "including" and/or "comprising" as used herein define the presence of stated features, integers, steps, operations, units and/or components without precluding the presence or addition of one or more other features, integers, steps, operations, units, components, and/or combinations thereof.

The present invention will be further described below with reference to the accompanying drawings and preferred embodiments.

As shown in FIG. 1, a method for visible cephalometric measurement is disclosed in this embodiment. The method includes:

S101: acquiring a data item to be measured according to a preset analysis method, and acquiring preset reference information;

S102: determining a measurement reference point according to the acquired preset reference information;

S103: generating a measurement result according to the measurement reference point and the data item to be measured, and displaying the measurement result.

The method for visible cephalometric measurement of the present invention includes the following steps: acquiring a data item to be measured according to a preset analysis method, and acquiring preset reference information; determining a measurement reference point according to the acquired preset reference information; and generating a measurement result according to the measurement reference point and the data item to be measured, and displaying it. In this way, based on the analysis method selected by the user, the data item to be measured is determined and the preset reference information is acquired according to the analysis method, then the measurement reference point is determined according to the acquired preset reference information, and the measurement result is generated according to the measurement reference point and the data item to be measured, and is displayed, so that the computer may automatically generate measurement results and perform cephalometric measurement more easily, accurately, and efficiently. When it is used, the user only needs to select the analysis method, and the system may determine the data items to be measured and the preset reference information according to the analysis method selected by the user, so as to prompt the reference point and other information for the user to select. After the user confirms, the reference point and other information may be referenced for measurement in order to obtain the measurement results.

Wherein, the preset analysis method includes at least one of the Tweed analysis method, Downs analysis method, Steiner analysis method, Wylie analysis method, Coben analysis method, Ricketts analysis method, quadrangular analysis method and soft tissue analysis method.

The Tweed analysis method mainly measures the triangles of the maxillofacial triangles that represent the facial morphological structure consisting of the Ohr-Augen-Ebene (or Frankfurt horizontal plane), the mandibular plane, and the long axis of the lower incisor. Ohr-Augen-Ebene-Mandibular Plane Angle (FMA): The angle between the Ohr-Augen-Ebene and the mandibular plane, and the tangent to the lower jaw margin serves as the mandibular plane. Lower Incisor—Ohr-Augen-Ebene Angle (FMIA): The angle between the long axis of the lower incisor and the Frankfurt plane. Lower incisor—mandibular plane Angle (IMPA): The angle between the long axis of the lower incisor and the mandibular plane.

The Downs analysis method uses the Ohr-Augen-Ebene as a reference plane, and specifically includes the following measurement contents:

(1) Measurement of bone-to-bone relationship: 1) facial angle: The lower back corner of facial plane intersecting with the Ohr-Augen-Ebene. This angle represents the degree of protrusion or contraction of the mandible. The larger the angle is, the more the mandible protrudes forward. On the contrary, it means the mandible contracts backward. 2) Angle of convexity: the intersection angle of NA and PA extension line. This angle represents the relationship of the facial maxilla to the entire facial side. When the PA extension line is in front of the NA, this angle is a positive value, whereas if the PA extension line is behind the NA, this angle is a negative value. The larger the angle is, the greater the relative convexity of the maxilla is, and vice versa. 3) AB plane angle: the intersection angle of AB or its extension line and facial plane. This angle represents the mutual positional relationship between the superior and inferior alveolar base bones. This angle has a negative angle before the facial plane, whereas it has a positive angle after the facial plane. The larger the angle, the greater contraction backward for the relative position of the maxillary base bone to the mandibular base bone; and the smaller the angle, the greater the relative position of the maxillary base bone to the mandibular base bone protrudes forward. 4) MPA. mandibular*plane angle: the intersection angle between the mandibular plane and the Frankfort plane angle (MP-FH). The mandibular plane is represented by a line tangent to the lower edge of the mandibular angle through the menton. This angle indicates the gradient of the mandibular plane and the height of the face. 5) Y-axis (Y axis) angle: The lower inner angle of the Y axis intersecting with the Ohr-Augen-Ebene. This angle also represents the protrusion and contraction of the chin region. The Y axis also represents the growth and development direction of the face.

(2) Measurement of the relationship between occlusion and skeleton: 1) a cant of an occlusion plane: the angle at which the occlusal plane intersects with the Ohr-Augen-Ebene. This angle represents the slope of the occlusal plane. The larger the angle is, the steeper the occlusal plane is. This is the Angle II facial type tendency. On the other hand, the smaller the angle is, the more flat the occlusal plane is. This is the Angle III facial type tendency. The occlusal plane uses marked point groups of the first permanent molar teeth and the upper and lower incisors. 2) Inter-incisal angle (1 [TXX-] to 1 [TX-] angle): The intersect angle between the long axes of the upper and lower incisors. This angle represents the convexity relationship between the upper and lower incisors. The larger the angle is, the smaller the convexity is; and the smaller the angle is, the greater the convexity is. The long axis of tooth is represented by the connecting line between the margin and the apex. 3) Lower incisor-mandibular plane angle (1 [TX-] to mandibular plane): The intersect angle between the long axis of the lower incisor and the mandibular plane. This angle indicates the faciolingual inclination of the lower incisor. 4) Lower incisor—ooclusal plane angle (1 [TX-] to occlusal plane): The lower front angle, which the long axis of the lower incisor intersects with the ooclusal plane. This angle represents the relationship between the lower incisor and the functional plane. 5) Upper incisor bulge distance (1[TX-]-AP): The vertical distance (mm) from the margin of the upper incisor to the AP connection line. This distance represents the degree of protrusion of the upper incisor and it is positive when the margin of the upper incisor is in front of the AP connection line, and instead, it is negative.

The Steiner analysis method, 1) sella-nasion-A point (SNA) angle: anterior basion plane-subspinale angle. It represents the positional relationship of the maxillary base bone to the cranium.

2) sella-nasion-B point (SNB) angle: anterior basion plane—supramental angle. It represents the positional relationship of the mandibular base bone to the cranium.

3) ANB angle: subspinale-nasion-supramental angle. This angle is the difference between the SNA and SNB angles and represents the positional relationship between the maxillary and the mandibular base bone.

4) SND angle: The angle formed by the anterior basion plane—the osseous mandible joint midpoint. It represents the positional relationship of the entire mandible to the cranium.

5) U1 [TXX-]-NA (mm): The vertical distance from the margin of the upper incisor to the NA connection line.

6) U1 [TXX-]-NA angle: The intersect angle between the long axis of the upper incisor and the NA connection line. It represents the degree of inclination and protrusion of the upper incisor.

7) L1 [TX-]-NB (mm): The vertical distance from the margin of the lower incisor to the NB connection line. This distance also represents the degree of convexity of the lower incisor.

8) L1 [TX-]-NB corner: The intersect angle between the margin of the lower incisor and the NB connection line. It represents the degree of inclination and protrusion of the lower incisor.

9) Po-NB (mm): The vertical distance from the pogonion to the NB connection line.

10) U1 [TXX-]-L1 [TX-] angle: The intersect angle between the long axes of upper and lower incisors.

11) OP-SN: The intersect angle between the occlusal plane and the anterior basion plane. It represents the slope of the occlusal plane.

12) GoGn-SN: the intersect angle between the mandibular plane and the anterior basion plane. It represents the slope of the mandibular plane and the height of the face. The mandibular plane consists of the connection line of the gonion and the gnathion.

13) SL (mm): The distance between the intersection points of vertical line from the sella turcica point to the pogonion to the SN plane. It represents the positional relationship of the mandibular chin region to the basion.

14) SE (mm): The distance between the intersection points of vertical line from the sella turcica point to the last point of the condylion to the SN plane. It represents the positional relationship of the mandibular condylion to the basion.

The Wylie analysis method is a measurement of the depth and height of the dentofacial morphological structure. All measurements are mainly line distance measurements. The facial depth measurement uses the sella turcica point as the measurement coordinate. The Ohr-Augen-Ebene is taken as the reference plane. A vertical line is drawn from the sella turcica center and individual marked points to be measured to the Ohr-Augen-Ebene. The distance between the foot of the marked points and the foot of the sella turcica point is measured. Alternatively, the distance between the foots of the marked points is measured.

(1) Condylion posterior tangent- sella turcica center (co-s): A vertical line is drawn from the posterior edge of the condylion and the sella turcica center perpendicular to the Ohr-Augen-Ebene. The distance between the two foots represents the mandible position.

(2) Sella turcica center-pterygomaxillary fissure (Ptm-S): The distance from the vertical line of the sella turcica center to the vertical line of the pterygomaxillary fissure. It represents the position of the maxillary.

(3) Maxillary Length (ANS-Ptm): The distance between the vertical line of the pterygomaxillary fissure and the vertical line of the anterior nasal spine.

(4) Pterygomaxillary fissure-first permanent molar (Ptm-6 [TXX-]): The distance between the vertical line of the pterygomaxillary fissure and the vertical line of the maxillary first permanent molar buccal groove. It is used to represent the location of the upper dental arch.

(5) Mandible length: This measurement is not in the Ohr-Augen-Ebene but in the mandibular plane. A line perpendicular to mandibular plane is tangentially drawn from the condylion posterior edge. And a line perpendicular to mandibular plane is tangentially drawn from the pogonion. The distance between the two perpendicular lines is measured.

(6) N-Me: The distance from the nasion to the menton.

(7) N-ANS: The distance from the nasion to the anterior nasal spine.

(8) ANS-Me: The distance from the anterior nasal spine to the menton.

(9) N-ANS/N-Me×100%: Percentage of the upper face height in overall height.

(10) ANS-Me/N-Me×100%: Percentage of the lower face height in the overall height.

The Coben analysis method includes the following measurement contents: Ba-N; Ba-A including Ba-S, S-Ptm, Ptm-A distances; Ba-Pog including Ba-Ar, Ar-Go, Go-Pog distances; N-Me including N-ANS, ANS-UI, UI-LI, LI-Me, ANS-Me distances; N-Go including N-S, S-Ar, Ar-Go, S-Go distances; mandibular ramus length (AL) and mandibular body length (MP).

The Ricketts analysis method includes the following measurement contents: facial angle, XY axis angle, A point protrusion, upper incisor bulge distance, lower incisor bulge distance, and inclination of the lower incisor.

The quadrilateral analysis method was proposed by Di Paool in the 1960s. The basic idea of this method is: as a normal person with facial coordination, the maxilla base bone length and the mandible base bone length=ANS-Me+ S-Go/2±1.5 (mm). It is characterized by the establishment of human face lower ⅓ skeletal structures on the basis of individualization. The structure and position of the maxillary bone and the mandibular bone are analyzed using line distance ratios and angles.

The soft tissue analysis method: With the development of soft tissue X-ray cephalometric techniques, there are more and more soft tissue analysis methods and measurement items. In 1985, Bishara analyzed various soft tissue analysis methods and summarized six commonly used soft tissue measurement items. During the longitudinal study of the soft tissue profile, the six measurement items were applied for analysis and good results were obtained.

Specifically, the preset analysis method in this embodiment includes a custom analysis method, and the custom analysis method is determined according to preset measurement data items. The user selects the measurement method built in the system or customizes a new measurement method according to his measurement habits and the actual situation of the patient.

In this embodiment, the preset reference information includes a preset reference point and name of the preset reference point; the step of determining a measurement reference point according to the obtained preset reference information specifically includes:

marking a preset reference point on a trace diagram according to the name of the preset reference point;

obtaining the reference point marked on the X-ray photograph and marking it on the corresponding reference point name. In this way, the user may be prompted to perform the operation of reference point marking. The user only needs to use the mouse to perform a click confirmation on the X-ray photograph. The user may also freely make a change.

For example in this embodiment, the method further includes:

marking the next preset reference point on the trace diagram according to the next preset reference point name. This allows users to quickly mark reference points and improve work efficiency.

In the present embodiment, after the step of acquiring the reference point marked on the X-ray photograph, the method further includes: acquiring a coordinate value of the reference point. In this way, the reference point may be located more accurately and the measurement result is more accurate.

Figure 2:
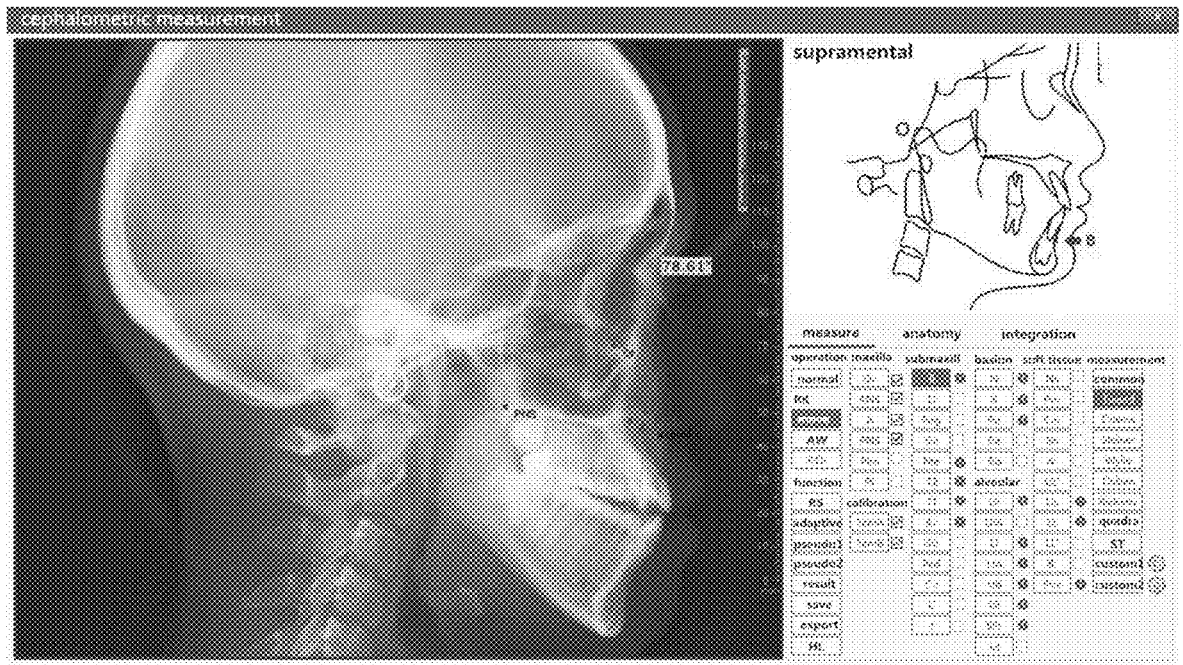
FIG. 2 is a first schematic diagram of an operation of a visible cephalometric system according to an embodiment of the present invention.
Figure 3:
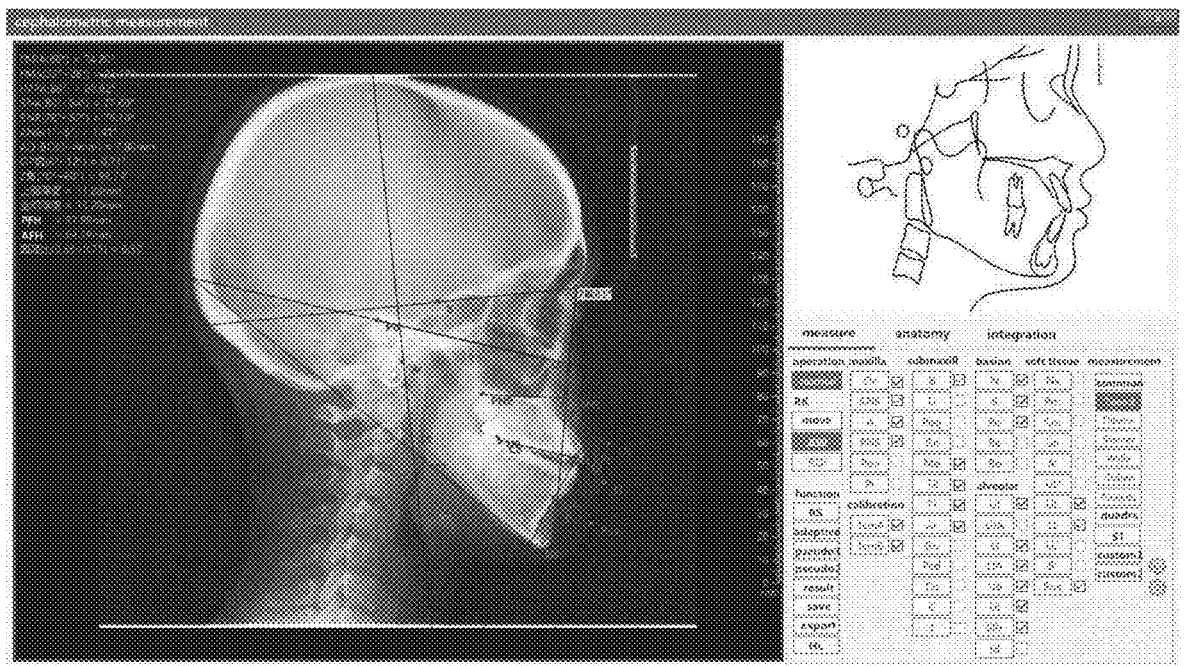
FIG. 3 is a second schematic diagram of an operation of a visible cephalometric system according to an embodiment of the present invention.

In this embodiment, not only the commonly used eight analysis methods (Tweed, Downs, Steiner, Wylie, Coben, Ricketts, quadrangular analysis, soft tissue analysis) but also the function of custom analysis method are provided. The doctor may customize the measurement method according to his own measure habit and the actual situation of the patient. This design is more convenient for the dental doctors' personalized treatment plan. Since each analysis method needs to locate dozens of reference points, it is easy to be confused during positioning, resulting in a wrong position. For this system, the reference point name and position indication are set, and doctors do not have to worry about the occurrence of the wrong point or the wrong position. When performing marking, the doctor only needs to click the left mouse button on the X-ray lateral cephalometrics based on the reference point name and position indication given by the system to complete the marking. For each mark of a reference point, the system will mark the corresponding point in the list ("√") and automatically jump to the next reference point to be marked. As shown in FIG. 2, the doctor does not need to manually select the next point to be measured. This arrangement may save the time for the doctor to think about measurement points, as well as shorten the measurement time. If the doctor accidentally misplaces the reference point, he may recalibrate the marked point at any time, and does not need to clear the other reference point positions. This design is more user-friendly and more convenient. At the same time, the system uses the scale setting method to eliminate the line-distance amplification error. After the reference point corresponding to the selected measurement method is marked, the system may automatically convert the marked points into coordinate values to perform calculations in order to ensure the accuracy of the data, as shown in FIG. 3. The system's automatic calculations not only provide unparalleled rapidity and convenience that manpower cannot achieve, but also eliminate the error of manual marking and measurement, increase the accuracy of measurement, and may better assist diagnosis and formulate a reasonable treatment plan, observe the therapeutic effect and prognosis; it may greatly improve the doctor's work efficiency and scientific accuracy of diagnosis.

Figure 4:
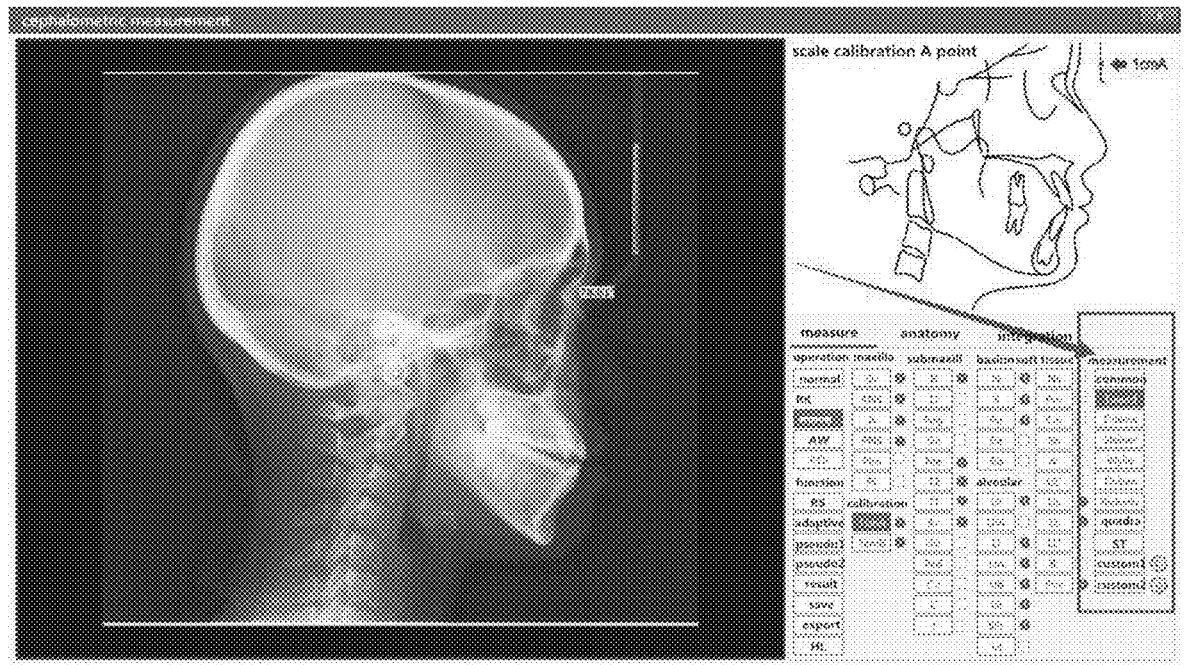
FIG. 4 is a third schematic diagram of an operation of a visible cephalometric system according to an embodiment of the present invention.

In order to meet the needs of different users, the system not only provides eight internationally-used analysis methods (Tweed, Downs, Steiner, Wylie, Coben, Ricketts, quadrilateral analysis, and soft tissue analysis) but also provides custom analysis functions. The two most commonly used custom analysis methods may be saved, as shown in FIG. 4.

Figure 5:
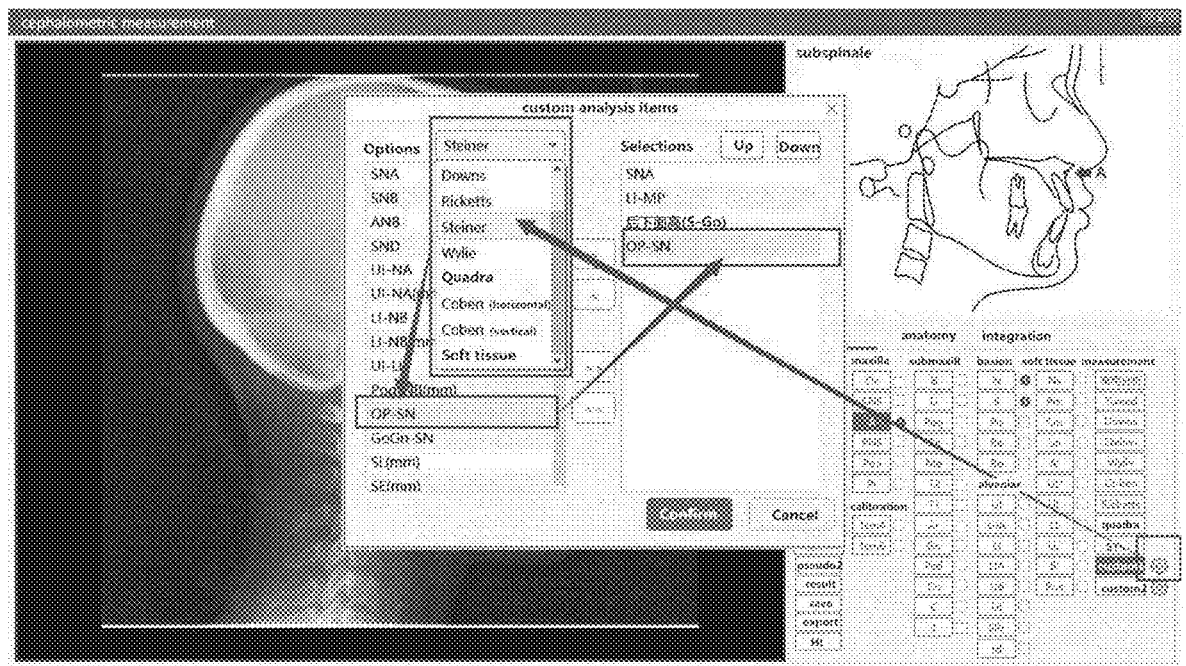
FIG. 5 is a fourth schematic diagram of an operation of a visible cephalometric system according to an embodiment of the present invention.

The doctor may define a measurement method according to his own measurement habits and the actual situation of the patient. The specific operation method is as shown in FIG. 5. First click the setup button. On the popup page, select a measurement method. Then select the desired items from the list of analysis items corresponding to the selected measurement method. The user may select different items in different measurement methods at the same time, and click to confirm after selection, then a custom measurement method is generated. The invention starts from the doctors' work habits and allows doctors to use it more conveniently.

Figure 6:
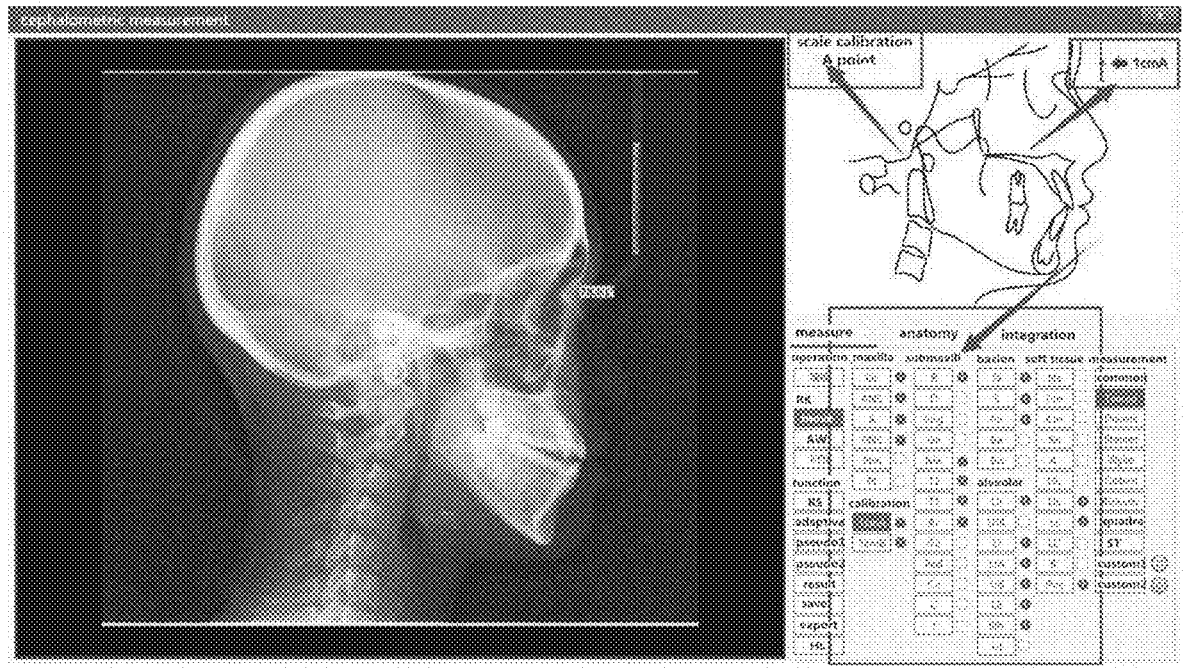
FIG. 6 is a fifth schematic diagram of an operation of a visible cephalometric system according to an embodiment of the present invention.

The system adds an anatomical structure trace diagram to the measurement page. After the doctor selects the measurement method, the system will automatically mark the reference point that needs to be calibrated. The name of the reference point and the position of the reference point that need to be calibrated will be displayed on the trace diagram one by one, as shown in FIG. 6.

Figure 7:
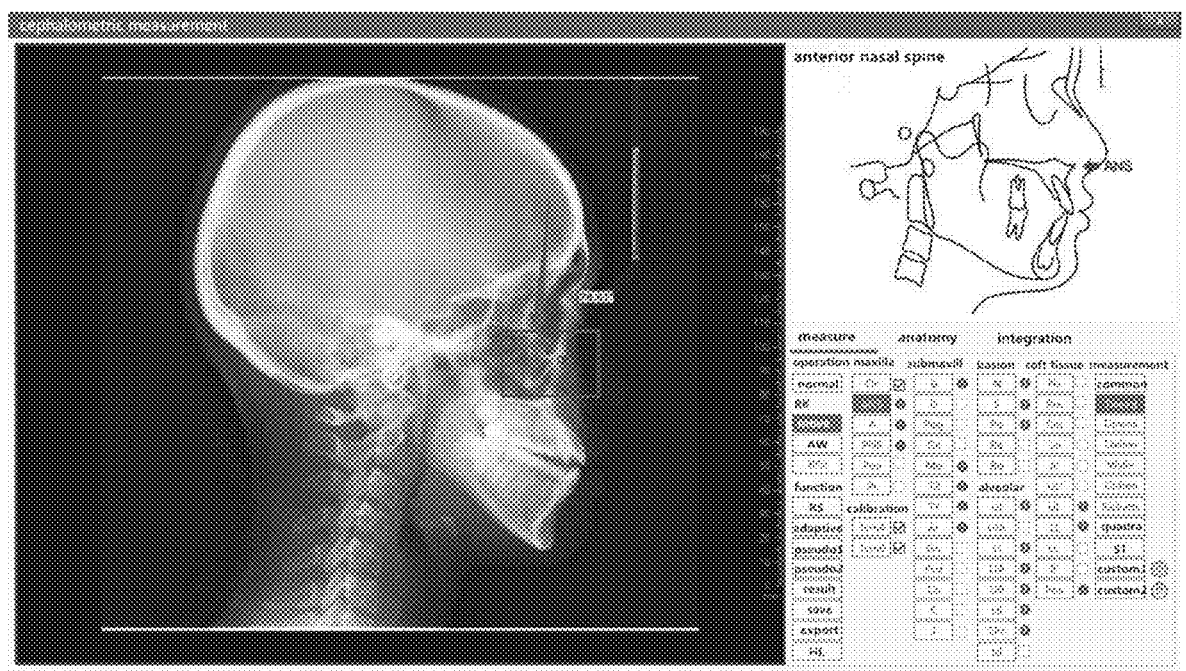
FIG. 7 is a sixth schematic diagram of an operation of a visible cephalometric system according to an embodiment of the present invention.

Marking the reference point according to the system's prompts, the user only need to find the position corresponding to the reference point on the image, and then click the left mouse button to complete the marking of the reference point, as shown in FIG. 7. In the process of determining the marked points, the amplification, brightness, and contrast of the image may be adjusted. For example, the soft tissue boundaries in the gray image may be unclear, pseudo color processing may be performed to improve the visibility of the image content, and interested region may also be selected to increase accuracy, in order to facilitate the marking or calibration of the reference measurement points.

Figure 8:
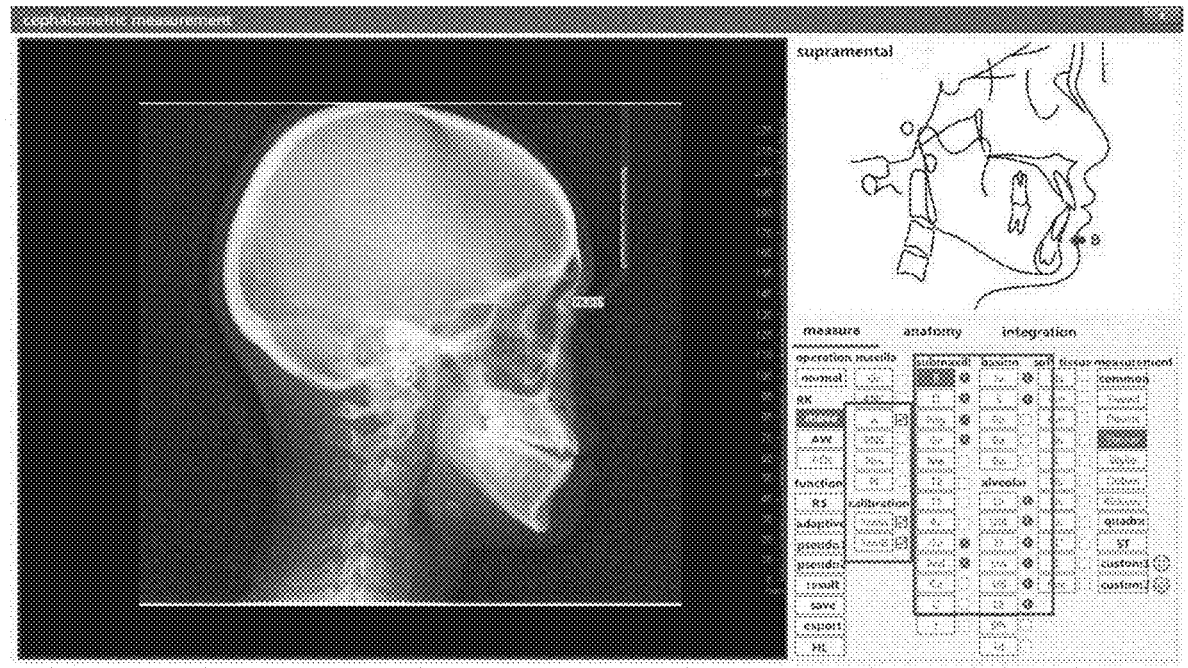
FIG. 8 is a seventh schematic diagram of an operation of a visible cephalometric system according to an embodiment of the present invention.

When the user selects the measurement method, the system will automatically mark the reference point to be measured. After the locating point is completed, the reference point will be marked with the positioned marker "√", and the system will automatically jump to the next reference point to be measured and prompt the user, without the user thinking about the next reference point to be located. As shown in FIG. 8.

Figure 9:
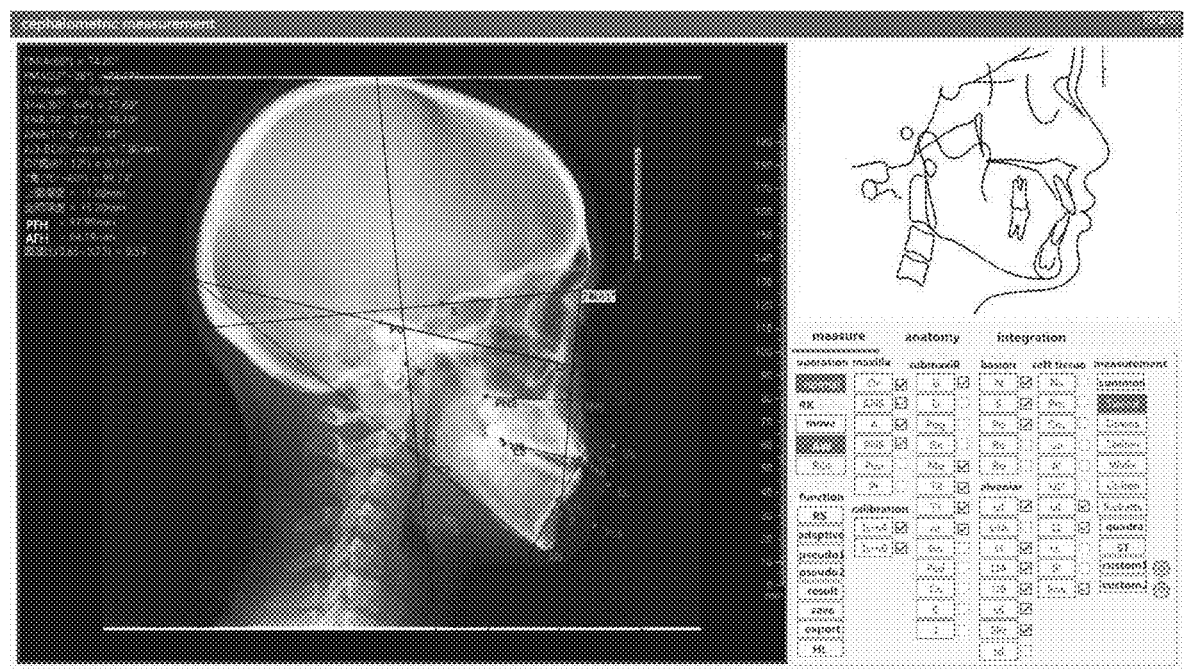
FIG. 9 is a eighth schematic diagram of an operation of a visible cephalometric system according to an embodiment of the present invention.

When the user completes calibration or marking of all the reference points, the system automatically generates a measurement report. As shown in FIG. 9.

A computer processing device is disclosed in this embodiment. The computer processing device includes a processor and a computer-readable storage medium. The processor obtains the computer programs on the computer-readable storage medium and performs the steps of any one of the foregoing methods.

Figure 10:
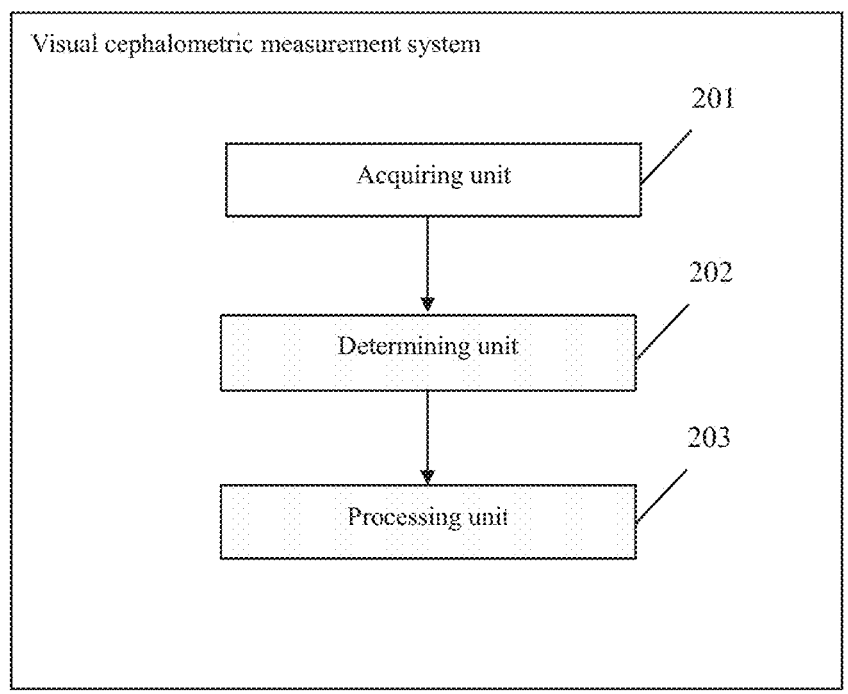
FIG. 10 is a schematic diagram of a visible cephalometric system according to an embodiment of the present invention.

As shown in FIG. 10, a visible cephalometric measurement system disclosed in this embodiment includes:
  an acquiring unit 201, configured to acquire a data item to be measured according to a preset analysis method, and acquire preset reference information;
  a determining unit 202, configured to determine a measurement reference point according to the acquired preset reference information;
  a processing unit 203, configured to generate a measurement result according to the measurement reference point and the data item to be measured, and display it.

In this way, according to the analysis method selected by the user, the data item to be measured is determined, the preset reference information is acquired, then the measurement reference point is determined according to the acquired preset reference information, and the measurement result is generated according to the measurement reference point and the measurement data item to be measured, and displays them, so that the computer may automatically generate measurement results and perform cephalometric measurement more easily, accurately, and more efficiently. When it is used, the user only needs to select the analysis method, and the system may determine the data items to be measured and the preset reference information according to the analysis method selected by the user, so as to prompt the reference point and other information for the user to select. After the user determines, the reference point and other information may be referred for measurement. And the measurement results are obtained.

Specifically, the preset reference information includes the preset reference point and the name of the preset reference point; the determining unit is specifically configured to: mark a preset reference point on a trace diagram according to a preset reference point name; obtain the reference point marked on the X-ray photograph and mark it on the corresponding reference point name.

The embodiment further includes a display unit for displaying an X-ray photograph, a trace diagram, a data item to be measured, a reference point name, and a measurement result. This facilitates the visible operations for the user and provides measurement efficiency.

The above content is a further detailed description of the present invention in combination with specific preferred embodiments, and it cannot be assumed that the specific implementation of the present invention is limited to these descriptions. For a person skilled in the art, a number of simple deductions or substitutions may be made without departing from the concept of the present invention, and should all be considered as falling within the protection scope of the present invention.

We claim:

1. A method for visible cephalometric measurement, comprising:
  acquiring, using a processor, at least one data item of a facial morphological structure according to a customized measurement method, the customized measurement method generated by selecting desired items from a list of cephalometric analysis items corresponding to at least one preset analysis method, wherein the at least one preset analysis method comprises calculating an intersect angle between an occlusal plane and an anterior basion plane representing a slope of the occlusal plane;
  based on the customized measurement method, displaying at least one preset reference point with a name of the at least one preset reference point and a position of the at least one preset reference point on an X-ray photograph of the facial morphological structure on a display screen one by one;
  obtaining a mark on the position of the at least one preset reference point on the X-ray photograph according to the name of the at least one preset reference point and a position indication of the at least one preset reference point;
  marking a corresponding point in the list of cephalometric analysis items and jumping to a next reference point;
  generating a measurement report of at least the marked corresponding point; and using the measurement report to correct surgical orthodontic prediction.

2. The method for visible cephalometric measurement according to claim 1, wherein the at least one preset analysis method comprises at least one of Tweed analysis method, Downs analysis method, Steiner analysis method, Wylie analysis method, Coben analysis method, Ricketts analysis method, quadrangular analysis method, and soft tissue analysis method.

3. The method for visible cephalometric measurement according to claim 1, wherein the generating of the customized measurement method comprises:
 selecting the at least one preset analysis method;
 selecting the desired items from the list of cephalometric analysis items corresponding to the selected at least one preset analysis method; and
 selecting different desired items in different preset analysis methods at a same time.

4. The method for visible cephalometric measurement according to claim 1, furthering comprising:
 adding an anatomical structure trace diagram to a measurement page of a measurement system which applies the method.

5. The method for visible cephalometric measurement according to claim 1, after the step of obtaining the mark on the position of the at least one preset reference point on the X-ray photograph, the method further includes:
 acquiring a coordinate value of the at least one preset reference point on the X-ray photograph.

6. A computer processing device including a processor and a computer-readable storage medium, wherein the processor acquires a computer program on the computer-readable storage medium and executes a method, comprising:
 acquiring, using a processor, at least one data item of a facial morphological structure according to a customized measurement method, the customized measurement method generated by selecting desired items from a list of cephalometric analysis items corresponding to at least one preset analysis method, wherein the at least one preset analysis method comprises calculating an intersect angle between an occlusal plane and an anterior basion plane representing a slope of the occlusal plane;
 based on the customized measurement method, displaying at least one preset reference point with a name of the at least one preset reference point and a position of the at least one preset reference point on an X-ray photograph of the facial morphological structure on a display screen one by one;
 obtaining a mark on the position of the at least one preset reference point on the X-ray photograph according to the name of the at least one preset reference point and a position indication of the at least one preset reference point;
 marking a corresponding point in the list of cephalometric analysis items and jumping to a next reference point;
 generating a measurement report of at least the marked corresponding point; and
 using the measurement report to correct surgical orthodontic prediction.

7. The computer processing device according to claim 6, wherein the at least one preset analysis method comprises at least one of Tweed analysis method, Downs analysis method, Steiner analysis method, Wylie analysis method, Coben analysis method, Ricketts analysis method, quadrangular analysis method* and soft tissue analysis method.

8. The method for visible cephalometric measurement according to claim 6, after the step of obtaining the mark on the position of the at least one preset reference point marked on the X-ray photograph, the method further includes:
 acquiring a coordinate value of the at least one preset reference point on the X-ray photograph.

9. A non-transitory computer-readable medium storing computerized code that when executed by an electronic device comprising memory and one or more processors, causes the processor to:
 acquire, using a processor, at least one data item of a facial morphological structure according to a customized measurement method, the customized measurement method generated by selecting desired items from a list of cephalometric analysis items corresponding to at least one preset analysis method, wherein the at least one preset analysis method comprises calculating an intersect angle between an occlusal plane and an anterior basion plane representing a slope of the occlusal plane;
 based on the customized measurement method, display at least one preset reference point with a name of the at least one preset reference point and a position of the at least one preset reference point on an X-ray photograph of the facial morphological structure on a display screen one by one;
 obtain a mark on the position of the at least one preset reference point on the X-ray photograph according to the name of the at least one preset reference point and a position indication of the at least one preset reference point;
 mark a corresponding point in the list of cephalometric analysis items and jumping to a next reference point;
 generate a measurement report of at least the marked corresponding point; and
 using the measurement report to correct surgical orthodontic prediction.

* * * * *